US010537320B2

(12) United States Patent
Bourque et al.

(10) Patent No.: US 10,537,320 B2
(45) Date of Patent: Jan. 21, 2020

(54) ARTICULATING NEEDLE

(71) Applicant: Smith & Nephew, Inc., Memphis, TN (US)

(72) Inventors: Bernard J. Bourque, Rehoboth, MA (US); David J. Callaghan, Waltham, MA (US)

(73) Assignee: Smith & Nephew, Inc., Memphis, TN (US)

( * ) Notice: Subject to any disclaimer, the term of this patent is extended or adjusted under 35 U.S.C. 154(b) by 96 days.

(21) Appl. No.: 15/547,976

(22) PCT Filed: Feb. 4, 2016

(86) PCT No.: PCT/US2016/016572
§ 371 (c)(1),
(2) Date: Aug. 1, 2017

(87) PCT Pub. No.: WO2016/126946
PCT Pub. Date: Aug. 11, 2016

(65) Prior Publication Data
US 2018/0021035 A1    Jan. 25, 2018

Related U.S. Application Data

(60) Provisional application No. 62/111,798, filed on Feb. 4, 2015.

(51) Int. Cl.
*A61B 17/04* (2006.01)
*A61B 17/06* (2006.01)

(52) U.S. Cl.
CPC .... *A61B 17/0401* (2013.01); *A61B 17/06066* (2013.01); *A61B 17/06109* (2013.01);
(Continued)

(58) Field of Classification Search
CPC .......... A61B 17/06066; A61B 17/0401; A61B 17/8872; A61B 2017/0409;
(Continued)

(56) References Cited

U.S. PATENT DOCUMENTS 4,719,924 A * 1/1988 Crittenden ...... A61M 25/09033
600/434
5,928,252 A   7/1999 Steadman et al.
(Continued)

FOREIGN PATENT DOCUMENTS

| WO | 2007124773 A1 | 11/2007 |
| WO | 2013163173 A1 | 10/2013 |
| WO | 2014043703 A1 | 3/2014 |

OTHER PUBLICATIONS

International Search Report and Written Opinion from related PCT Application No. PCT/US2016/016572 dated Apr. 26, 2016.
(Continued)

*Primary Examiner* — Diane D Yabut
*Assistant Examiner* — Majid Jamialahmadi
(74) *Attorney, Agent, or Firm* — Burn & Levinson, LLP; Joseph M. Maraia

(57) ABSTRACT

An arthroscopic needle having partial cuts or serrations along one side of a circular, hollow needle shaft allows the needle to bend, or articulate, by drawing a pull strip bar, defined by a thin strip along the interior side closet to the serrations in the hollow shaft, for compressing along the cuts to draw uncut segments into closer arrangement for curving the needle in the direction of the compressed side. The selectively articulating, or "bendable" needle that curves in response to a rotating knob provides for insertion of surgical attachment anchors in difficult-to-reach areas of meniscal tissue. The disclosed articulating needle has the ability to
(Continued)

bend and access more anterior and posterior zones of meniscal repairs than conventional rigid needle approaches.

12 Claims, 5 Drawing Sheets

(52) U.S. Cl.
CPC ............... *A61B 2017/0409* (2013.01); *A61B 2017/0414* (2013.01); *A61B 2017/0419* (2013.01); *A61B 2017/0464* (2013.01); *A61B 2017/061* (2013.01); *A61B 2017/0608* (2013.01)

(58) Field of Classification Search
CPC ...... A61B 2017/061; A61B 2017/0419; A61B 2017/22022; A61B 2017/22095; A61M 25/0133; A61M 25/0138; A61M 25/0147; A61M 25/0141; A61M 25/0144; A61M 2025/015; A61M 2025/009
See application file for complete search history.

(56) References Cited

U.S. PATENT DOCUMENTS

| | | | |
|---|---|---|---|
| 6,059,719 A | 5/2000 | Yamamoto | |
| 6,156,044 A | 12/2000 | Naik | |
| 6,543,456 B1 | 4/2003 | Freeman | |
| 7,179,267 B2 | 2/2007 | Robertson | |
| 8,128,640 B2 | 3/2012 | Harris et al. | |
| 8,808,309 B2 | 8/2014 | Nelson et al. | |
| 9,402,616 B2 | 8/2016 | Harris et al. | |
| 2001/0025134 A1* | 9/2001 | Bon | A61M 25/0136 600/146 |
| 2002/0188301 A1 | 12/2002 | Amery | |
| 2005/0033363 A1 | 2/2005 | Bojarski et al. | |
| 2007/0219464 A1* | 9/2007 | Davis | A61M 25/0138 600/585 |
| 2008/0249483 A1* | 10/2008 | Slenker | A61B 1/0055 604/275 |
| 2009/0182354 A1 | 7/2009 | Blier | |
| 2010/0106169 A1 | 4/2010 | Niese et al. | |
| 2012/0130173 A1* | 5/2012 | Lutze | A61B 1/00071 600/146 |
| 2014/0305988 A1 | 10/2014 | Baxter, III | |
| 2015/0190129 A1 | 7/2015 | Nelson et al. | |
| 2017/0027557 A1 | 2/2017 | Harris et al. | |

OTHER PUBLICATIONS

EP Office Action for EP App No. 09764137.7 dated Aug. 16, 2017, 6 pages.
IPRP for PCT/US2016/016572 dated Aug. 8, 2017, 7 pages.
Chinese Application No. 201680008998.7 Text of the First Office Action dated Aug. 29, 2019.
Chinese Application No. 201680008998.7 Search Report.

\* cited by examiner

ARTICULATING NEEDLE

CROSS-REFERENCE TO RELATED APPLICATIONS

This is a U.S. National Stage application under 35 U.S.C. 371 of co-pending International Application No. PCT/US2016/016572, filed Feb. 4, 2016, and entitled "ARTICULATING NEEDLE," which claims priority to U.S. Provisional Application Ser. No. 62/111,798, entitled "ARTICULATING NEEDLE" and filed on Feb. 4, 2015, the entire contents of which are hereby incorporated herein by reference.

BACKGROUND

Arthroscopic knee procedures often employ suture attachments to meniscal tissue for repairing tears or injury to the human meniscus. Due to the complex nature of a knee joint, as well as various locations on the curved meniscal tissue that may need to be accessed, insertion of surgical instruments can be difficult. Meniscal tissue is more firm than epidermal (skin) tissue, and substantial force is required to pierce the meniscal tissue, typically for insertion of a suture anchor or "T", aptly named for the appearance of a "T" when the suture extends from the middle of a rigid crossmember. Surgeons must often navigate around anatomical structures such as the Anterior Cruciate Ligament (ACL) and Medial Collateral Ligament (MCL), and may need to approach the meniscal tissue from a variety of angles. A rigid curvature of a needle for meniscal repair aids in piercing the meniscal tissue and inserting the anchor, however may interfere when passing the curved needle past other anatomical structures such as the ACL and MCL.

SUMMARY

An arthroscopic needle having partial cuts or serrations along one side of a circular, hollow needle shaft allows the needle to bend, or articulate, by drawing a pull strip bar, defined by a thin strip along the interior side closet to the serrations in the hollow shaft, for compressing along the cuts to draw uncut segments into closer arrangement for curving the needle in the direction of the compressed side. The selectively articulating, or "bendable" needle that curves in response to a rotating knob provides for insertion of surgical attachment anchors in difficult-to-reach areas of meniscal tissue. The disclosed articulating needle has the ability to bend and access more anterior and posterior zones of meniscal repairs than conventional rigid needle approaches.

Curvature of a needle for meniscal repair aids in piercing the meniscal tissue and inserting the anchor, however may interfere when passing the curved needle past other anatomical structures such as the ACL and MCL. An articulated needle has a controllable curve section, or articulated section, that responds to rotation of an articulating knob on a proximate end of the needle outside the surgical site. The articulated section curves, or articulates, following insertion adjacent to the meniscal tissue for achieving an insertion angle for piercing the meniscal tissue. A straightened needle is passed into the surgical site, avoiding unintended piercing of nearby anatomical structures, and then articulated for achieving the desired insertion angle.

In configurations discussed below, an arthroscopic needle employs partial cuts or serrations along one side of a circular needle shaft. The partial cuts allow the needle to bend, or articulate, by compressing along the cuts to draw separated segments into closer arrangement while the uncut side remains continuous, thus compressing cutaway voids for curving the needle in the direction of the compressed side.

In example embodiments, a surgical tool is disclosed the tool including a circular, hollow needle shaft; an articulating portion on the needle shaft having serrations defined by partial cuts adapted to draw uncut segments closer by closing a gap defining the cuts; a needle tip secured in the hollow portion at an end of the needle shaft adjacent the articulating portion; and a pull strip attached to the needle tip on a side corresponding to the serrations and adapted to pull the serrations together by closing a gap defined by the cuts, the closely drawn serrations causing the needle tip to articulate in the direction of the cuts resulting from the articulating portion of the needle being longer on an uncut side. In example embodiments, a method for utilizing the surgical tool may include inserting the articulating needle device to the surgical site and subsequently actuating the pull strip to achieve a desired articulation angle for the needle tip.

In some embodiments, the cuts may extend across the diameter of the hollow shaft. In further embodiments, the surgical tool may further include an articulating knob in threaded communication with the pull strip for effecting translational movement of the pull strip. In example embodiments, the serrations may be annular serrations and the cuts may include arcuate cutouts aligned along a traverse cross-section of the shaft. In some embodiments, the articulating portion of the needle shaft may be limited to a distal portion of the needle shaft proximal to the needle tip. Advantageously, in further embodiments, the tool may also include one or more stops or markings (e.g., along the pullstrip or relative to the turn knob) for enabling selection of a desired bend angle of the needle tip relative to the shaft.

In example embodiments, the pull strip bar may be baraligned along the side of the cannulated shaft. In some embodiments, the pull strip bar may pass through a cannulation in the shaft. For example, the shaft may include pull strip tubing supports for supporting the pull strip bar along the interior of the shaft. Advantageously, the pull strip tubing supports may separate the pull strip bar from an actuator extending through the cannulation in the shaft and configured for driving a surgical anchor through a channel in the needle tip. Thus, e.g., the pull strip tubing supports may be anchored offset from a cross-sectional center of the shaft. As noted above, in example embodiments the surgical tool may further include an actuator extending through a cannulation in the shaft and configured for driving a surgical anchor through a channel in the needle tip.

In further example embodiments, a surgical tool may include a cannulated needle shaft; an articulating portion of the needle shaft having serrations; a needle tip secured relative to the needle shaft proximal to the articulating portion; and an actuator adapted for at least one of (i) compressing or (ii) expanding the serrations thereby causing the needle tip to articulate. Advantageously, the serrations can include cutouts and/or slits. Similar to other embodiments, the actuator may include a pull strip attached to the needle tip on a side corresponding to the serrations.

In example embodiments, a surgical method for applying a surgical anchor to a surgical site utilizing a needle with an articulating tip is disclosed. The method may advantageously include inserting the needle while in a straight configuration and subsequently articulating the articulating tip of the needle once a target surgical site is reached; and utilizing the needle to pierce tissue at the target surgical site and to dispose the surgical anchor. In example embodiments, the surgical site may be at the knee joint and the inserting the needle while in a straight configuration may be utilized to get the needle past the ACL and MCL. In some embodiments, the surgical anchor may be disposed for the purposes of repairing the meniscus of the knee joint. In example embodiments, the method may further include determining an appropriate approach angle for use in piercing the tissue and selectively articulating the articulating tip to provide for the appropriate approach angle. Advantageously, the appropriate approach angle may be determined based at least in part on an insertion trajectory of the needle from a point of entry.

BRIEF DESCRIPTION OF THE DRAWINGS

The foregoing and other features will be apparent from the following description of particular embodiments disclosed herein, as illustrated in the accompanying drawings in which like reference characters refer to the same parts throughout the different views. The drawings are not necessarily to scale, emphasis instead being placed upon illustrating the principles of the invention.

DETAILED DESCRIPTION

Configurations disclosed below include an articulating needle device including an articulating section of a needle and a control mechanism for selectively articulating (bending) the articulating section. The needle employs a cannulated (hollow) shaft for passing through an actuator and a pull strip bar. The actuator substantially occupies a central region defining an axis through the cannulated interior, and the pull strip bar is defined by a thin strip along the interior side closet to the serrations in the hollow shaft.

A needle tip assembly is attached at a distal end of the shaft, and is attached (welded) to the pull strip bar. An opposed end of the pull strip bar is likewise welded to a lead screw at the proximate end of the tubing. Threads in the lead screw draw the pull strip bar upon rotation, applying tension to the needle tip along the serrated (cut) side of the shaft and drawing the serrated sections together to articulate the needle.

In an example configuration depicted below, the surgical tool includes a circular, hollow needle shaft, and an articulating portion on the needle shaft has serrations defined by partial cuts adapted to draw uncut segments closer by closing a gap defining the cuts. A needle tip is secured in the hollow portion at an end of the needle shaft adjacent to the articulating portion 110, and a pull strip bar is attached to the needle tip on a side corresponding to the serrations and adapted to pull the serrations together by closing a gap defined by the cuts. The resulting closely drawn serrations cause the needle tip to articulate in the direction of the cuts resulting from the articulating portion of the needle being longer on an uncut side. The cuts or serrations extend across the diameter of the hollow shaft, and may be varied to provide a resistance or bias to articulation. Since the uncut portions of the serrated diameter deform for providing the articulation angle, shallower cuts that leave more material will result in a stiffer articulating section 110 that requires greater force to articulate. The force is provided by an articulating knob in threaded communication with the pull strip for disposing the pull strip.

Figure 1:
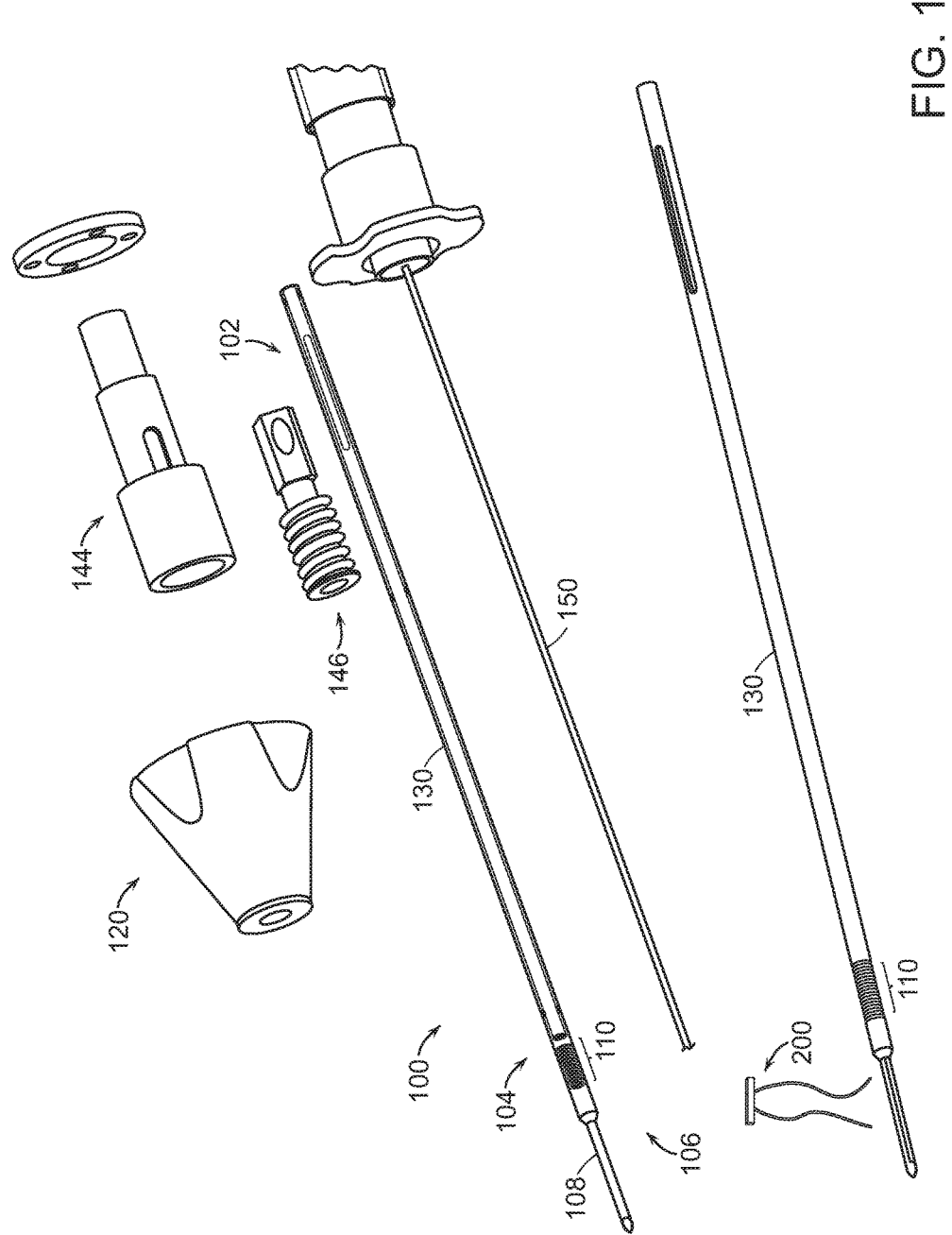
FIG. 1 is an exploded view of the articulating needle device.
Figure 2A:
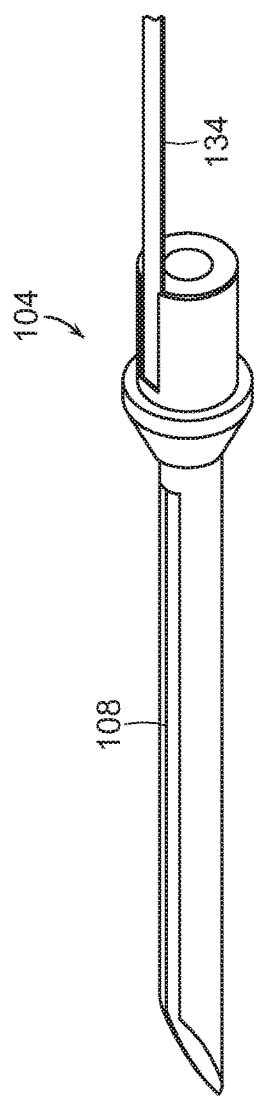
FIGS. 2a-2d show the articulating needle portion.
Figure 2B:
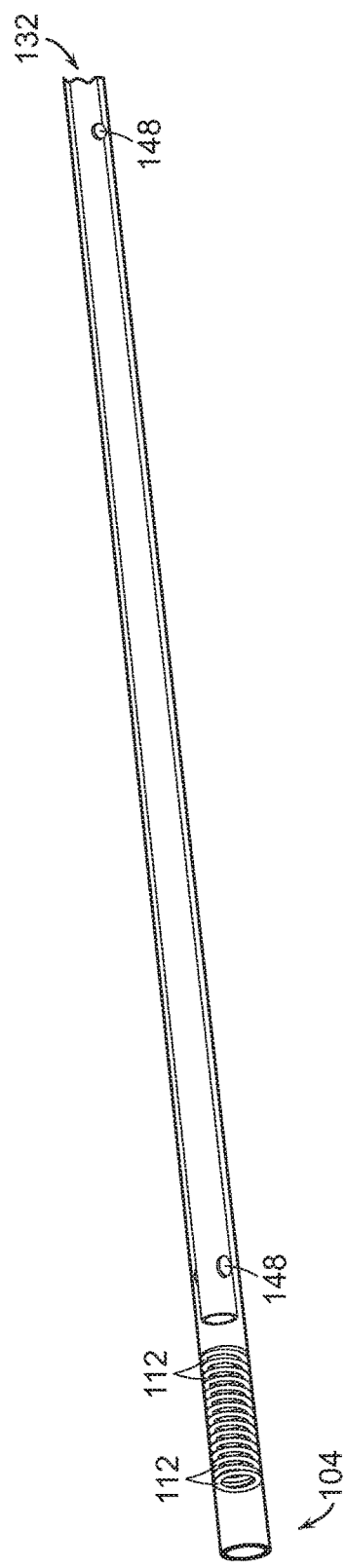
Figure 2C:
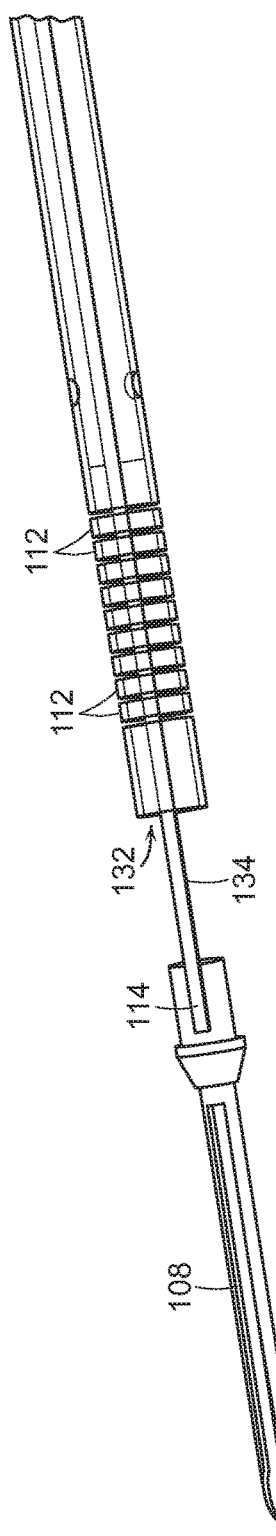
Figure 2D:
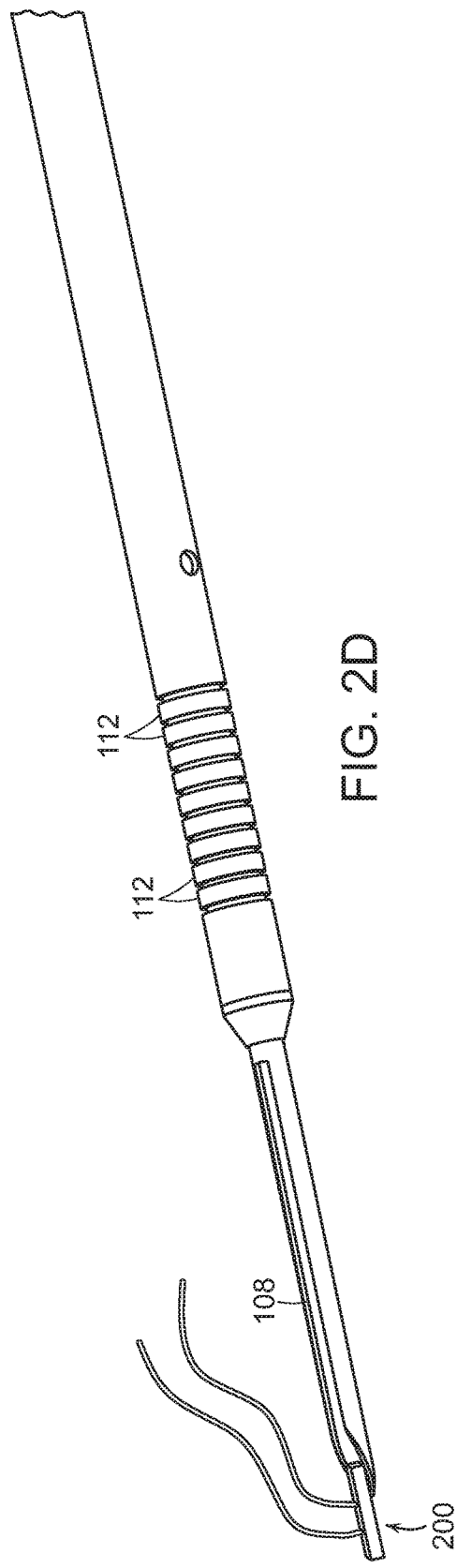

FIG. 1 is an exploded view of the articulating needle device. Referring to FIG. 1, an articulating needle 100 includes a controllable curve section 110 responsive to an articulating knob 120 adapted for rotation around a needle proximate end 102. The controllable curve section 110, or articulating section, includes a series of serrations 112 defined by partial cuts in a needle side 104. The cuts extend partially across the diameter at a needle distal end 106 such that a needle tip assembly 108 drawn by threaded actuation from the articulating knob causes the serrations to compress and close a cut region between the serrations and bend, or articulate the needle tip 108 in the direction of the needle side 104 having the serrations. Threaded engagement with a lead screw housing 144 causes a lead screw 146 to pull back on a pull strip bar 134 attached to the needle tip 108 on the needle side 104 having the serrations 112. The articulating needle 100 may advantageously be operatively associated with an anchor element (e.g., T anchor 200) such as for enabling insertion thereof.

FIGS. 2a-2d show the articulating needle portion. Referring to FIGS. 1 and 2a-2d, the needle tip 108 attaches to the pull strip bar 134 via welds 114. The pull strip baraligns along the side 104 of the cannulated shaft 130. A cannulation 132 accommodates the pull strip bar 134 along the side 104 so as not to interfere with an actuator 150 passed through the center of the cannulation 132. A set of tubing supports 148 disposes the pull strip bar 143 along the side 104 of the cannulation 132. Pull strip tubing supports 148 are defined by transverse members through the interior of the hollow shaft. The pull string tubing supports are anchored slightly above a cross-section center of the shaft, so as not to interfere with the actuator passed through the center axis. The pull strip supports 148 therefore are between the actuator and the pull strip bar 134 for supporting the pull strip bar along the interior of the shaft 130 on the serrated side 104. The actuator 150 is subsequently disposed forward for driving T anchors (e.g., T anchor 200) through a channel in the needle tip assembly 108. The channel in the needle tip assembly 108 is continuous with the cannulated center 132 of the shaft such that once the needle 108 pierces the meniscal tissue, advancement of the actuator 150 drives a T anchor (e.g., T anchor 200) through the pierced hole for securing on an opposed side of the meniscal tissue.

Figure 3A:
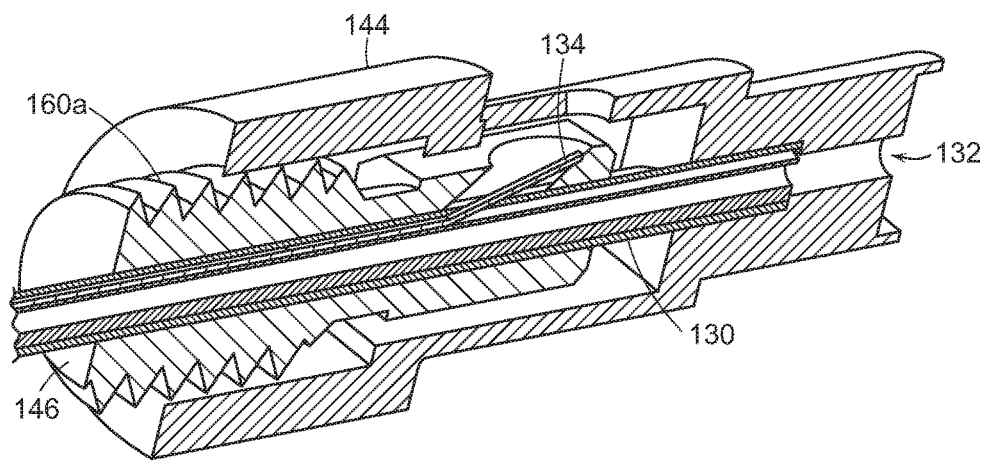
FIGS. 3a-3b show a threaded portion for controlling articulation.
Figure 3B:
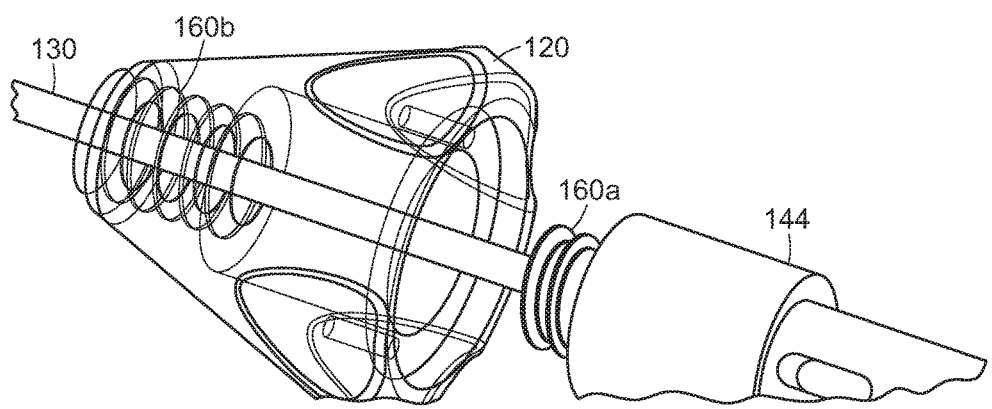

FIGS. 3a-3b show a threaded portion for controlling articulation. Referring to FIGS. 3a and 3b, the lead screw 146 has threads 160a that engage threads 160b on the articulating knob 120 for drawing the pull strip bar 134 towards the proximate end 102 of the shaft 130 as the lead screw housing 144 is drawn backwards. The cannulation 132 houses both the pull strip bar 134 and the guidewire 150.

Figure 4A:
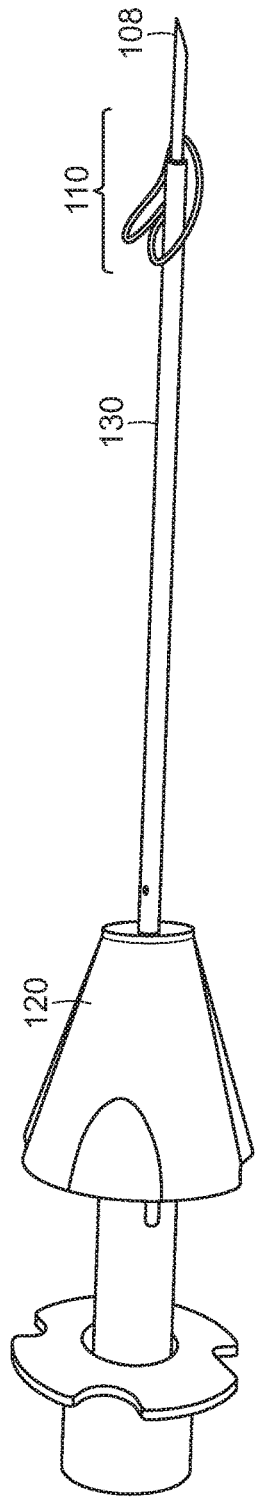
FIG. 4a shows the articulating needle in a straight (unarticulated) position.
Figure 4B:
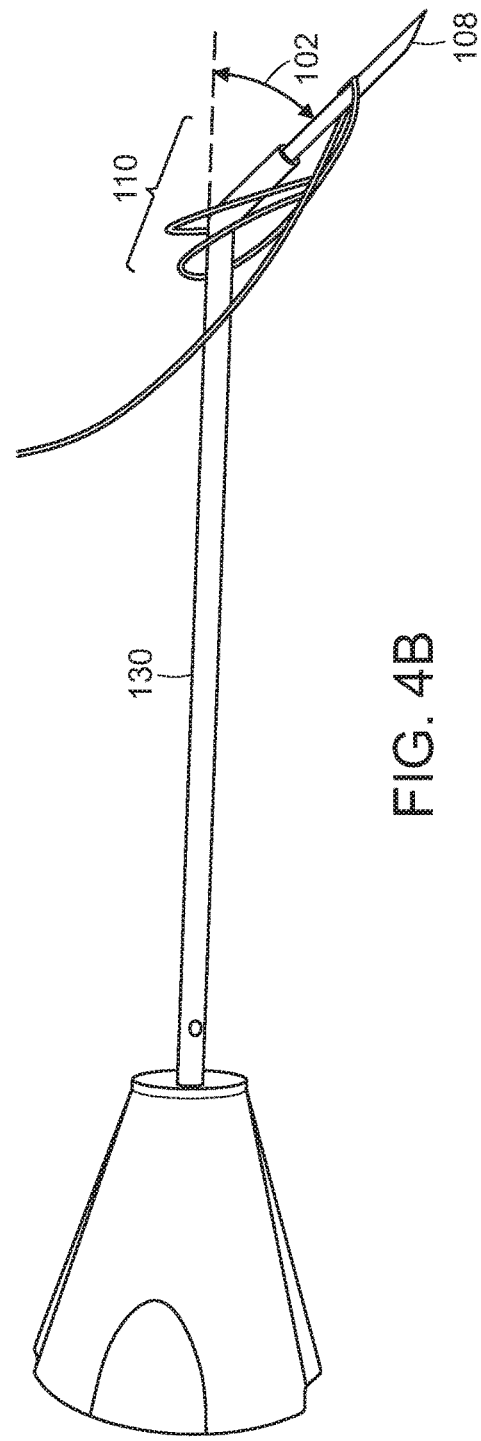
FIG. 4b shows the articulating needle in a curved (articulated) position.

FIG. 4a shows the articulating needle in a straight (unarticulated) position, and FIG. 4b shows the articulating needle in a curved (articulated) position. Referring to FIGS. 4a and 4b, the controllable curve section 110 articulates to "bend" the shaft 130 and attached needle section 108 by an insertion angle 102, as the articulating knob 120 rotates to draw the pull strip bar 134 back and compress the serrations 112 in the controllable curve section 110.

In operation of the articulating needle device, once the articulating needle is inserted to the surgical site, rotation of the articulating knob draws the lead screw back (toward the proximate end of the shaft) for achieving the desired articulation angle.

Previously disposed T anchors, typically two, have been loaded into the channel in the needle top assembly prior to surgical insertion. A surgeon inserts the needle through the meniscal tissue to pierce a slit sufficiently large to pass a transverse member of the T anchor. The actuator is slid forward for disposing the first T anchor through the slit, following which the transverse member lodges parallel to the opposed side of the meniscal tissue to form a perpendicular attachment for a suture attached to the middle of the transverse member. The procedure is repeated at a second location for inserting the second T anchor. Alternate configurations utilize a multi-stage insertion that has positive stops after each anchor deployment to prevent over-insertion and premature deployment, and is discussed further in a corresponding document.

It will be understood by those skilled in the art that various alternative embodiments, features and implementations of the above described example embodiments of the articulating needle may be employed without departing from the scope of the present disclosure. Some of these alternative embodiments, features and implementations are described in greater detail in the sections which follow.

In some embodiments, various alternative configurations of the serrations in the shaft may be employed. In particular, whereas in the depicted example embodiments the serrations utilize annular configuration (e.g., formed by transversely aligned arcuate cutouts/slits along a traverse cross-section of the shaft) other configurations may likewise be employed, without departing from the scope of the present disclosure. Thus, for example, in some embodiments, the serrations may feature a spiral serration pattern or a partial spiral serration pattern (e.g., formed by slanted/tilted arcuate cutouts/slits along angular cross-sections of the shaft. In further embodiments, the serrations may feature a combinations of patterns. For example, in some embodiments, transversely aligned arcuate cutouts/slits (e.g., which may be configured for effecting bending in a first direction) may be utilized in series with slanted/tilted cutouts/slits (configured for effecting bending in a second direction different from the first direction). In some embodiments, arcuate cutouts/slits be parallely aligned (e.g., so as to be substantially parallel to a same cross-sectional plane of the shaft, such as a same transverse or angular cross-sectional plane of the shaft). In example embodiments, parallely aligned arcuate cutouts/slits may be configured to effect bending in a same direction. Alternatively, progressively or differently angled arcuate cutouts/slits may be utilized wherein such cutouts may be configured to effect bending in a plurality of different directions at different longitudinal positions of the shaft (advantageously while utilizing compression/extension forces along a same first axis. Thus, advantageously in some embodiments, a bending of the articulating needle may be in different directions along different longitudinal positions of the shaft, thereby enabling a spiral or helical bending shape. Notably, a spiral or helical bend to the needle may advantageously enable progressing the needle tip through a target tissue by way of a rotation of the shaft.

As noted above, the serrations in the shaft may be characterized by cutouts and/or slits in the shaft. Notably, slits may be appropriate, for example for embodiments wherein the slits are subjected to expansion forces thereby effecting bending of the needle (whereas cutouts may advantageously be either compressed or expanded in order to effect bending of the needle).

In example embodiments, such as depicted in the Figures, arcuate cutouts along the shaft may be characterized by a uniform thickness along the length of arc. Alternatively in some embodiments, the arcuate cutouts may be characterized by a varying thickness, e.g., wherein one or more end sections of the arc include a narrower or tapered thickness relative to a middle section of the arc. Thus, in some embodiments, the cutouts may be characterized by an elliptical, trapezoidal, triangular, or other tapered shape, e.g., may be characterized by a tapered projective geometry. Advantageously, in some embodiments, the geometry of the cutouts may be configured to enable initial bending of the needle in a first direction followed by the needle bending in a second direction different than the first direction as the cutouts are compressed and/or expanded.

Although example embodiments of the disclosure are directed towards implementations involving compressive bending, e.g., wherein compressive forces may be applied to cutouts in the shaft in order to pull the serrations together by closing a gap defined by the cutouts (whereby the needle tip articulates in the direction of the cuts resulting from the articulating portion of the needle being longer on an uncut side), the present disclosure is not limited to such embodiments. Rather, it is appreciated that in some embodiments, extension bending may be utilized, e.g., wherein expansion forces may be applied to cutouts and/or slits in the shaft in order to expand the cutout and or slit by widening a gap defined by the cutout or slit (whereby the needle tip articulates in the direction opposite from the cuts resulting from the articulating portion of the needle being shorter on an uncut side). Notably, the compression bending and extension bending may each have their own distinct advantages. For example, compression bending may, inter alia, advantageously enable a more controlled bending process, e.g., based on the shape and/or orientation of the cutouts. Compression bending may also advantageously enabling controlling/preventing overbending of the needle. Conversely, with respect to extension bending, the use of slits as opposed to cutouts may advantageously facilitate easier insertion which the shaft is in a straight configuration (e.g., without catching on surrounding tissue). Moreover, expansion of cutouts as opposed to compression of cutouts may mitigate pinching of tissue during bending of the needle.

As depicted in the Figures, in some embodiments, a pull strip (along a longitudinal axis of the shaft and offset from a center) may be utilized to apply compression and/or expansion forces to a first side of the shaft. It will be appreciated, however by one of ordinary skill in the art that any number of different configuration may enable application of such compression and/or expansion forces. For example, in some embodiments, compression forces may be applied by means of a tightening a band or some other constrictive element around the serrated portion of the shaft. Similarly, in some embodiments, one or more wedge elements may be utilized to apply expansion forces.

Advantageously, compression and/or expansion forces may be applied along a first longitudinal axis of the shaft, e.g., offset from the center and extending along a first side of the shaft (e.g., extending longitudinally at a first radial position of the shaft's circumference). In some embodiments, a single compressions/expansion mechanism may be utilized for applying compression/expansion forces along the first longitudinal axis. In further embodiments a plurality of compression/expansion mechanisms may be utilized each configured for applying compression/expansion forces along a different longitudinal axis of the shaft. For example, in some embodiments, a first compression/expansion mechanism may be utilized for applying compression/expansion forces along a first longitudinal axis of the shaft (e.g., the first longitudinal axis being offset from the center and extending along a first side of the shaft such as extending longitudinally at a first radial position of the shaft's circumference). The first compression/expansion mechanism may be utilized in conjunction with or independent from a second compression/expansion mechanism configured for applying compression/expansion forces along a second longitudinal axis of the shaft different from the first longitudinal axis of the shaft (e.g., the second longitudinal axis being offset from the center and extending along a second side of the shaft such as extending longitudinally at a second radial position of the shaft's circumference). In some embodiments, the first and second longitudinal axes may be on opposite sides of the shaft (e.g., so as to enable bending of the needle in opposite directions). Alternatively, the first and second longitudinal axes may be offset from one another by 90 degrees (e.g., so as to enable bending of the needle along transverse dimensional axes such as selective bending of the needle along each of a first dimension and along a second dimension perpendicular to the first dimension). Advantageously, by selectively bending a needle along first and second dimensional axes one can selectively bend the needle in any desired/selected direction.

In some embodiments, such embodiments described above, the needle may be configured to effect pending in a pre-determined direction/orientation. In further embodiments, the needle may be configured to enable a user to control/select the direction/orientation of the bend (e.g., by way of utilizing some combination of a plurality of compression/expansion mechanisms). In some embodiments, a bend angle and/or shape may also be controlled/selected. For example, in some embodiments, the bend angle and/or shape may be controlled by way of controlling a degree of compression/expansion of the serrations. Thus, in some embodiments, a compression/expansion mechanism may include one or more stops, each corresponding to a particular bend angle and/or shape. In some embodiments, a stop may also be utilized to prevent over-bending of the needle. In further embodiments, a plurality of compression/expansion mechanisms may each control the bend angle and/or shape of the needle at different longitudinal positions of the needle. Thus, the overall shape and trajectory of the needle may be controlled by way of utilizing some combination of the plurality of compression/expansion mechanisms.

As described above, in some embodiments a turn knob may be used to actuate a compression/expansion mechanism (e.g., a turn knob may be utilized to cause translational movement of a pull strip). It will be appreciated, however, that the present disclosure is not limited to such embodiments. Rather, any number of different actuation mechanisms may be utilized. For example, in some embodiments, a ratchet mechanism may be used for controlling the translational movement of the pull strip. In example embodiments, a preload may be associated with the actuation mechanism, e.g., for facilitating applying the necessary bending forces to the needle such as by lowering a force threshold. Notably, in other embodiments, a preload may similarly be applied to the serrations, e.g., wherein the serrations are subject to compression/tension forces when the needle is in a straight configuration. This may similarly facilitate applying the necessary bending forces and/or may be utilized to further control bending of the needle.

Advantageous surgical methods are enabled by way of the disclosed articulating needle. For example, in some embodiments, the needle may be inserted while straight configuration and subsequently bent to facilitate use of the needle at the target site. This may be particularly applicable, e.g., with respect to meniscal repair and other knee applications, where a straight configuration of the needle may facilitate insertion of the needle past the ACL and MCL and proximal to the surgical site (e.g., the knee joint cavity) after which the needle is changed to a bent configuration. In particular, once at the surgical site an appropriate approach angle for the surgical procedure may be selected/determined, e.g., based on the particular insertion trajectory of the needle relative to the patient's anatomy. Thus, in example embodiments, the needle may be selectively bent once at the surgical site to provide the appropriate approach angle for the surgical procedure.

While the system and methods defined herein have been particularly shown and described with references to embodiments thereof, it will be understood by those skilled in the art that various changes in form and details may be made therein without departing from the scope of the invention encompassed by the appended claims.

What is claimed is:

1. A surgical tool comprising:
   a circular, hollow needle shaft, an articulating portion on the needle shaft having serrations defined by partial cuts;
   a needle tip secured in a hollow portion at an end of the needle shaft adjacent the articulating portion;
   a pull strip bar attached to the needle tip on a side corresponding to the serrations and adapted to closely draw the serrations together by closing a gap defined by the cuts, the closely drawn serrations causing the needle tip to articulate in the direction of the cuts; and
   an actuator extending through a cannulation in the needle shaft and configured for driving a surgical anchor through a channel in the needle tip.

2. The surgical tool of claim 1 wherein the cuts extend across the diameter of the needle shaft.

3. The surgical tool of claim 1 further comprising an articulating knob in threaded communication with the pull strip bar for effecting translational movement of the pull strip bar.

4. The surgical tool of claim 1 wherein the serrations are annular serrations and the cuts include arcuate cutouts aligned along a traverse cross-section of the needle shaft.

5. The surgical tool of claim 1 wherein the articulating portion of the needle shaft is limited to a distal portion of the needle shaft proximal to the needle tip.

6. The surgical tool of claim 1 wherein the tool includes one or more stops or markings for enabling selection of a bend angle of the needle tip relative to the shaft.

7. The surgical tool of claim 1 wherein the pull strip bar is baraligned along the side of the needle shaft.

8. The surgical tool of claim 1, wherein the pull strip bar passes through the cannulation in the needle shaft.

9. The surgical tool of claim 8, wherein the needle shaft includes pull strip tubing supports for supporting the pull strip bar along the interior of the needle shaft.

10. The surgical tool of claim 9, wherein the pull strip tubing supports separate the pull strip bar from the actuator.

11. The surgical tool of claim 9, wherein the pull strip tubing supports are anchored offset from a cross-sectional center of the needle shaft.

12. A method for utilizing the surgical tool of claim 1, the method comprising inserting the articulating needle device to the surgical site and subsequently actuating the pull strip bar to achieve a desired articulation angle for the needle tip.

* * * * *